United States Patent
Gefen

(10) Patent No.: US 9,173,568 B2
(45) Date of Patent: Nov. 3, 2015

(54) METHOD AND SYSTEM FOR DETECTING NEUROPATHY

(75) Inventor: Amit Gefen, Ganei Tikva (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 1008 days.

(21) Appl. No.: 13/148,704

(22) PCT Filed: Feb. 14, 2010

(86) PCT No.: PCT/IL2010/000131
§ 371 (c)(1),
(2), (4) Date: Aug. 10, 2011

(87) PCT Pub. No.: WO2010/092581
PCT Pub. Date: Aug. 19, 2010

(65) Prior Publication Data
US 2011/0313314 A1  Dec. 22, 2011

Related U.S. Application Data

(60) Provisional application No. 61/207,474, filed on Feb. 12, 2009.

(51) Int. Cl.
*A61B 5/00* (2006.01)
*A61B 5/04* (2006.01)
*A61B 5/01* (2006.01)

(52) U.S. Cl.
CPC ............... *A61B 5/0051* (2013.01); *A61B 5/441* (2013.01); *A61B 5/483* (2013.01); *A61B 5/4827* (2013.01); *A61B 5/01* (2013.01); *A61B 5/04001* (2013.01)

(58) Field of Classification Search
CPC .. A61B 5/04; A61B 5/04001; A61B 5/04002; A61B 5/04012; A61B 5/0051
USPC .......... 600/549, 555, 12; 607/48, 46
See application file for complete search history.

(56) References Cited

U.S. PATENT DOCUMENTS

| 4,653,507 A | 3/1987 | Laudadio |
| 5,002,065 A | 3/1991 | LaCourse et al. |

(Continued)

FOREIGN PATENT DOCUMENTS

| EP | 1 518 497 | 3/2005 | |
| EP | 1 625 841 | 2/2006 | |
| EP | 1 656 885 | 5/2006 | |
| EP | 1 749 588 | 7/2007 | |
| WO | WO 2005040989 A2 * | 5/2005 | .................. 607/134 |
| WO | WO 2006/046901 | 5/2006 | |

OTHER PUBLICATIONS

Atlas E., Yizhar Z., Khamis, S., Slomka, N., Hayek, S., Gefen, A., "Utilization of the foot load monitor for evaluating deep plantar tissue stresses in patients with diabetes: Proof-of-concept studies"; *Gait & Posture*, 2009, (29), 377-382.

(Continued)

*Primary Examiner* — Max Hindenburg
(74) *Attorney, Agent, or Firm* — Frommer Lawrence & Haug LLP; William S. Frommer

(57) ABSTRACT

The invention provides a system and method for detecting or monitoring neuropathy in an individual. The system of the invention includes a platform having a surface in which a plurality of stimulators is embedded. Each stimulator is configured to stimulate a region in a skin area when the skin area is applied to the platform. The stimulators may deliver thermal and/or vibrational energy to the skin region. In the method of the invention, a skin area is applied to platform and one of the stimulators is activated. A minimal stimulation is determined that is sensed by the individual in a skin region in contact with a stimulator. Neuropathy in the skin region in contact with the stimulator is detected if either the determined minimal stimulation is above a predetermined threshold, or if a stimulation is not sensed before a magnitude of the stimulation reaches a predetermined maximal magnitude. The process is then repeated with other stimulators.

32 Claims, 5 Drawing Sheets

(56) References Cited

U.S. PATENT DOCUMENTS

| | | | |
|---|---|---|---|
| 5,007,433 | A | 4/1991 | Hermsdorffer et al. |
| 5,022,407 | A | 6/1991 | Horch et al. |
| 5,191,896 | A | 3/1993 | Gafni et al. |
| 5,381,805 | A | 1/1995 | Tuckett et al. |
| 5,666,963 | A | 9/1997 | Swenson et al. |
| 6,090,050 | A | 7/2000 | Constantinides |
| 2003/0152133 | A1 | 8/2003 | Ellenz |
| 2005/0075669 | A1 | 4/2005 | King |
| 2005/0131317 | A1* | 6/2005 | Oddsson et al. ............... 600/592 |
| 2007/0139167 | A1* | 6/2007 | Gilson et al. ............... 340/407.1 |

OTHER PUBLICATIONS

Krishnan, S. T. M., Rayman, G., "The LDIflare: A novel test of C-fiber function demonstrates early neuropathy in type 2 diabetes", *Diabetes Care*, 2004, (27), v. 12, (2930-2935).

Van Schie, C.H.M., "A review of the biomechanics of the diabetic foot", *International Journal of Lower Extremely Wounds* 4,3, 2005, p. 160.

Gefen, A. "Plantar soft tissue loading under the medial metatarsals in the standing diabetic foot", *Medical Engineering & Physics* 25, 2003, 491-499.

* cited by examiner

METHOD AND SYSTEM FOR DETECTING NEUROPATHY

FIELD OF THE INVENTION

This invention relates to medical devices, and more specifically to devices for detecting neuropathy.

BACKGROUND OF THE INVENTION

The following prior art references are considered as being relevant for an understanding of the invention.

Atlas E, Yizhar Z, Khamis S, Slomka N, Hayek S, Gefen A. Utilization of the foot load monitor for evaluating deep plantar tissue stresses in patients with diabetes: Proof-of-concept studies. Gait Posture, 29:377-82, 2009.

Gefen A. 2003. Plantar soft tissue loading under the medial metatarsals in the standing diabetic foot. Med Eng Phys. 25:491-9.

Krishnan S T M, Rayman G. 2004. The LDlflare: A novel test of C-fiber function demonstrates early neuropathy in type 2 diabetes. Diabetes Care 27: 2930-5.

van Schie C H. 2005. A review of the biomechanics of the diabetic foot. Int J Low Extrem Wounds. 4:160-70.

U.S. Pat. No. 4,653,507 to Laudio.
U.S. Pat. No. 5,191,896 to Gafni.
U.S. Pat. No. 5,007,433 to Hersdorffer.
U.S. Pat. No. 5,666,963 to Swenson et al.
U.S. Pat. No. 6,090,050 to Constantinides.

Diabetic neuropathy is a peripheral nerve disorder caused by diabetes and is considered to be the most common serious complication of the disease. Diabetic neuropathy typically evolves in multiple locations, and induces damage to numerous peripheral nerves. Pathological changes to the nerves occur both in the body of axons and in myelin sheaths. Initially, the axons become thin and the myelin sheaths start to disintegrate, thereby slowing the conduction velocity in the affected nerves. Subsequently, the complete nerve structure is atrophied. While these changes occur systematically across the nervous system, they are most profound in the distal regions of the somatic nerves. This condition is referred to as poly-neuropathy and affects the arms, hands, fingers, legs, and feet. Loss of sensation in the feet is the most common symptom. This loss of sensation is manifested in numbness or insensitivity to pain or temperature. The loss of sensation in the feet is associated with progressive foot deformities, such as hammertoes and the collapse of the midfoot. Blisters and ulcers may appear on numb areas of the foot because sustained mechanical loading (pressure, shear) and even actual injury go unnoticed. If foot injuries are not treated promptly, infection may occur that spreads sub-dermally and into the bone. Sustained mechanical loads in deep tissues also occur, and may lead to ulcers (Gefen, 2003; Atlas et al., 2009). Progressive ulcers often require amputation of the toes or the entire foot.

Diabetic foot ulcers are relatively common, and are estimated to occur in 15% of the diabetic population, which is estimated at about 150 million people worldwide today. It is estimated that half the amputations caused by diabetic neuropathy are preventable when minor problems are caught and treated in time, particularly if the patient is aware of his/her neuropathy condition.

Apart from foot ulcers, the continuous numbness and tingling of the hands and feet also decrease the quality of life for patients with diabetes. Unfortunately, at present, once nerve damage occurs, it is irreversible. Symptoms are often minor at first, and because most nerve damage occurs over several years, mild cases may go unnoticed for a long time, but can suddenly become severe. The key issue in managing diabetes in general, and in managing diabetic neuropathy in particular, is prevention of further damage to tissues and organs by using medications and a diet to control the level of glucose and avoid hyperglycemia.

The clinical practice for preventing diabetic foot ulcers is to protect the feet by prescribing high quality, well fitting footwear, preferably custom-made footwear. In order for this approach to work, patients at risk need to be identified, and their footwear needs to be carefully designed to protect the most vulnerable regions on the patient's feet by re-distributing mechanical loads onto other, less susceptible foot areas. This is commonly done by first measuring pressures under the patient's feet. However, it is the localization of neuropathy, as opposed to the level of pressure, which is the most important predictor of possible ulceration (van Schie, 2005).

Screening for the presence of neuropathy using standard, simple clinical tools, such as the neuropathy disability score, neuropathy symptom score, pressure perception using Semmes-Weinstein monofilaments and vibration sensation with the neurothesiometer (marketed by Horwell Scientific Laboratory Supplies, Nottingham, UK) has been shown to be important in identifying individuals at risk for foot ulceration. However, these tools assess mainly large fiber function (Krishnan and Rayman, 2004). It has been suggested that small unmyelinated C-fibers, which are responsible for sensating heat (responsive from 30 to over 45° C.), may be selectively damaged in the early stages of diabetes (Krishnan and Rayman, 2004).

The most commonly used method for diagnosing peripheral neuropathy today is the Semmes-Weinstein method. As known in the art, the Semmes-Weinstein monofilament consists of a nylon filament embedded in a plastic handle that is used to assess semi-quantitatively the threshold sensitivity for light touch by exploiting physical properties of a buckling column to theoretically generate a force independent of the force applied to the handle. The actual pressure delivered to the skin surface in fact varies with the angle between the filament and the skin. Moreover, the friction between the filament and skin is not considered in the measurement, but may vary considerably among individuals, thereby introducing an inherent error into these measurements. Most importantly, the Semmes-Weinstein monofilament test is able to estimate a rough range of sensitivities, as opposed to a specific sensitivity of the individual.

An alternative method applies a two-point static touch to the skin surface. This test measures how far apart two separate touch points need to be for the touch points to be perceived as two distinct points. The tip of the test device is composed of two parallel pin pricks whose separation can be adjusted. Like the Semmes-Weinstein test, the two point test is affected by the orientation of the pricks with respect to the skin, and by the friction between the device and the skin. Also, the sensation threshold depends on the magnitude of pressure applied by the examiner over the tested tissue region.

Another method uses a calibrated tuning fork or a vibration perception threshold meter (biothesiometer). The volume of vibration of a vibrating tip attached to the skin is raised until the patient feels the vibration. The vibration perception threshold is measured in volts. The major problem with the biothesiometer devices is that they produce a wave, as opposed to a local stimulus. The vibratory wave propagates over a relatively large area of skin and subcutaneous tissues, thereby making it extremely difficult to identify the location of the most severe neuropathy, where tissues need to be protected.

Another method uses a pen-shaped device having a polymer surface and a metal alloy surface. The polymer surface feels warmer than the metal alloy due to the difference in thermal conductivity of the materials. The examiner randomly places one of the two surfaces on the top of the patient's foot and asks whether it feels cold or not so cold at that particular spot. This does not provide a quantitative reading, and therefore does not allow systematic comparisons with normative databases. Additionally, because the device is a passive thermal element, its performance will depend on ambient conditions (the manufacturer recommends using it in a room below 23° C.). Since the device is pressed against the patients' skin during examination, the local perception of temperature is masked by the perception of pressure. A commercially available device that uses this method is the "tip-therm"® device (by tip therm GmbH).

Another method uses a single heat stimulator that is strapped around a specific location on the foot or hand (e.g. using Velcro straps wrapped around the foot or hand). Once fixated and turned on, the stimulator heats up to a pre-determined temperature which can be adjusted, usually up to 50° C. A patient response device, typically containing press-buttons labeled "Yes" and "No", is used by the patient to indicate whether or not he can feel the warm sensation, and if yes, for how long, which is the time during which the "Yes" button is pressed. The output of the system is a comparison of the time during which heating was actually applied by the stimulator strapped to the skin, against the time length of stimulation reported by the patient. The single stimulator only provides a measure of the neuropathy at the specific spot where it is attached, and so, neuropathic sites could be missed. Also, the stimulator is mechanically strapped to the skin, which induces uncontrolled mechanical loads on the examined area (and these loads are also not necessarily physiological). The temperature sensation is therefore often masked by the pressure sensation because of the strapping. Examples for commercial devices employing this method are the Computer Aided Sensory Evaluator—IV (CASE IV) (WR Medical Electronics, Stillwater, Minn., USA) and the TSA-II Neuro-Sensory Analyzer (Medoc Advanced Medical Systems, Ramat Vishay, Israel).

Another method for detecting peripheral neuropathy is to test the responsiveness of the sweat glands of the feet, which cease to function normally when neuropathy develops. This is done by employing a chemical reaction of cobalt salt ($CoCl_2$) with moisture. If moisture from sweat exists, a pad containing $CoCl_2$ that is adhered to a spot on the plantar foot changes color from blue to pink. This is a qualitative indicator rather than quantitative, that the assessment of neuropathy is indirect, i.e. no actual sensation is measured. The indication is limited to the spot where the pad is located, and that the test is biased by humid environments. A commercial product that uses this method is the Neuropad® (miro Verbandstoffe, Wiehl-DrabenderhOhe, Germany).

Thus, existing devices that apply a thermal stimulus on the skin to assess neuropathy are either hand-held (e.g. the Semmes-Weinstein, the two-point touch, the biothesiometer devices) or strapped to the skin surface (e.g. the TSA-II system). With these devices, the force, angle of application and speed at which they are used to assess the neuropathy, are highly variable among examiners.

U.S. Pat. No. 4,653,507 to Laudio discloses a device comprising a first thermal conductive sensing plate having a fixed temperature and a second thermal conductive sensing plate having a controllable temperature. The plates are applied to the skin and the threshold temperature differential between the plates is determined.

U.S. Pat. No. 5,191,896 to Gafni et al discloses an apparatus in which sensory stimulation is applied to a patient in accordance with any one of several protocols.

U.S. Pat. No. 5,007,433 to Hersdorffer discloses a pressure stimulator configured to apply a selectable pressure to a skin surface.

U.S. Pat. No. 5,666,963 to Swenson et al discloses a hand-held device which is translated or rolled over a skin surface. The contact surface on the device is made of a high thermal conductivity material, and when the device is at room temperature, a cooling sensation is experienced by the subject except in those regions where nerve sensation is abnormally low.

U.S. Pat. No. 6,090,050 to Constantinides discloses a device for recording temperatures on a skin surface.

Prior art devices evaluate temperature perception of the skin at a single site per examination. Hand-held stimulators tend to be inaccurate because the pressure applied to the skin surface varies from user to user which often affects the local perception of temperature changes.

SUMMARY OF THE INVENTION

The present invention provides a method and system for detecting or monitoring neuropathy over a skin area. The invention further allows mapping of the neuropathy over the skin surface. The skin area may be on a body extremity, such as a foot or hand. The system of the invention comprises a rigid platform in which a plurality of stimulators is embedded. In the case of a foot examination, the subject stands on the platform, or sits so that his feet are resting on the platform, so as to apply at least parts of the soles of his feet to the array of stimulators. In the case of a hand examination, the subject places his palm or palms on the platform. The stimulator may comprise a heating element, in which case the stimulation delivered by the stimulation is thermal energy. Alternatively, the stimulator may comprise a vibrator, in which case the stimulation delivered by the stimulator is a vibrational energy. In another embodiment of the invention, the stimulator comprises a heating element and a vibrator, in which case thermal energy and vibrational energy may be delivered by the stimulator, either simultaneously or sequentially.

In the method of the invention, after application of one or more skin areas to the platform, one of the stimulators in the platform is selected, and is activated with the magnitude of the stimulation made to gradually increase. The subject is instructed, as soon as the subject feels a sensation in his skin, to indicate where in his skin he senses the sensation. This may be done by providing a screen showing a diagram of the contours of the skin areas under examination, and instructing the subject to either touch the screen at the location in the diagram corresponding to the location in the skin where he senses the sensation or to indicate the location using any other feedback means such as a handheld pointing device such as a mouse, trackball, touchpad, joystick, pressure stick, light pen or light gun, or using eye tracking, or using voice commands. In the case of thermal stimulation, the difference between the initial temperature of the skin before the heating commenced and the temperature at that location at the time of the patient's response is recorded. This differenced is referred to as the "detectable temperature difference" (DTD) and is a measure of the localized heat perception of the subject. In the case of vibrational stimulation, the magnitude of the vibration of the stimulator at the time of the patient's response is recorded. This magnitude of the vibration is referred to as the "detectable vibration magnitude". If a predetermined magnitude of the stimulation of the stimulator has been reached without the subject indicating detection of a heating and/or vibrational sensation, or if the subject indicates an incorrect location, then a record is made indicating that the stimulus was not detected by the subject. During the examination, the subject does not receive feedback whether his report on location was correct, or what the extent of his sensitivity to the stimulation was. This recorded stimulation represents the minimal sensation sensible by the subject at the skin region in contact with the selected stimulator. The process is preferably repeated until all stimulators in contact with the subject's skin have been heated, in a random or non-random order.

The system and method of the invention do not involve strapping sensors to the skin surface, or manually applying sensors to the skin surface. The sensitivity data are acquired under physiological loading (standing on the platform or sitting so that the platform serves as a footrest for a foot examination, and resting the hands on the platform for a hand examination), which tends to reduce or eliminate variability in the response due to variability in the pressure to which the hands or feet are applied to the stimulators, as occurs when sensors are strapped to the skin surface or are manually applied to the skin surface.

The invention thus allows testing neuropathy under physiological loading, to avoid mixture of patients' perceptions of temperature or vibration and pressure, and also, to avoid inter-operator variations. For foot examination, it is preferable that the patient stands on the stimulators rather than pressing a measurement tool against the feet using a non-controlled, examiner-dependent force. Also, deformation of the nerves, when subjected to bodyweight, may affect the perception of sensation, which is yet another reason why neuropathy should be diagnosed under physiological mechanical loading (e.g. on the sole of the foot, while a patient is standing).

The invention allows assessment of the threshold for sensation by gradually increasing the magnitude of the stimulation of a skin region. Thermal receptors, for example, are most active during a change of temperature. A static primary thermal sensation fades away by rapid neural adaptation, as is experienced when a person gets into a hot tub. Hence, it is favorable to detect the localized responsiveness to heating while the skin is subjected to a time-dependent temperature rise.

The invention may be used to monitor the course of the neuropathy, to determine the effect of a drug or treatment on the course of the neuropathy, and to select the most appropriate drug or treatment for the neuropathy.

Thus, in one of its aspects, the invention provides a system for detecting or monitoring neuropathy comprising a platform, the platform comprising a surface in which a plurality of stimulators are embedded, each stimulator configured to stimulate a region in a skin area when a skin surface is applied to the platform.

In another of its aspects, the invention provides a method for detecting or monitoring neuropathy comprising:
(a) applying at a skin area to a platform, the platform comprising a surface in which a plurality of stimulators is embedded, each stimulator configured to stimulate a skin region when a skin surface is applied to the skin region;
(b) activating at least one of the stimulators;
(c) determining a minimal stimulation at which a stimulation is sensed in a skin region in contact with a stimulator;
(d) comparing the determined minimal stimulation to predetermined threshold stimulation;

(e) detecting neuropathy in the skin region in contact with the stimulator if (i) the determined minimal stimulation is above the predetermined threshold, or (ii) if a stimulation is not sensed in the skin region in contact with the stimulator before an magnitude of the stimulation reaches a predetermined maximal temperature;
(f) repeating steps (b) to (e) as required, each time selecting a different stimulator.

The invention also provides a method for monitoring the effect of a drug on neuropathy in an individual, comprising:
(a) detecting a first extent of the neuropathy in the individual by the method according to any one of claims 16 to 30;
(b) administering the drug to the individual; and
(c) detecting a second extent of the neuropath after administration of the drug to the individual.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
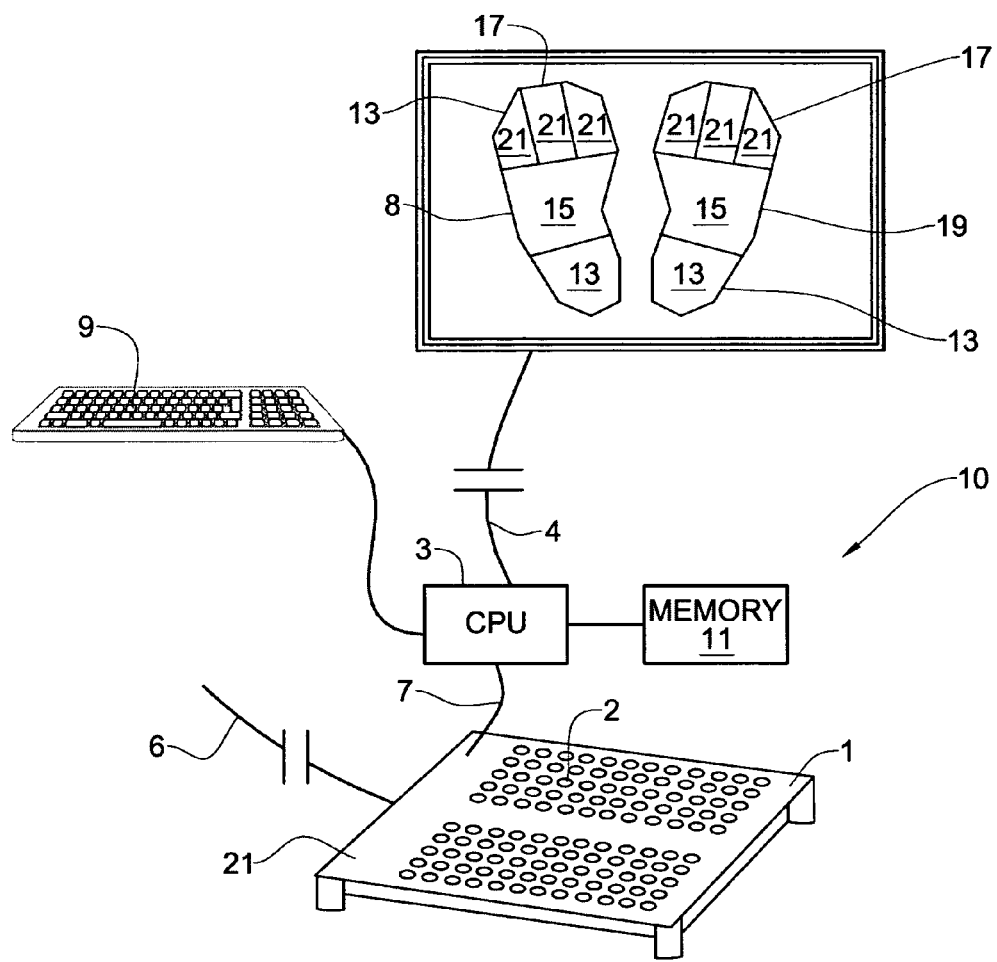
FIG. 1 shows a system for detecting neuropathy in accordance with one embodiment of the invention.

FIG. 1 shows a system 10 for mapping neuropathy in one or more skin areas in accordance with one embodiment of the invention. The system 10 comprises a rigid platform 1 upon which one or more skin areas, such as foot or hand surfaces are applied, as described in detail below. The platform 1 has a surface 21 made from a thermally insulating material, such as hard rubber or plastic, in which a plurality of stimulators 2, also described below, are embedded. The surface 21 may be a planar surface. The activity of each stimulator is under the control of a computer processing unit (CPU) 3 which communicates with the stimulators 2 via a communication line 7 which may be a wired link or a wireless link. A user data input device, such as a key board 9, a computer mouse or a voice recognition system, is used to input relevant data to a memory 11 associated with the CPU 3, such as an identification of the subject, or the skin areas applied to the surface 21. The system 2 further comprises a user feedback device that allows the subject to indicate where and when a heating sensation is detected. The system may include a display 5 showing a diagram of the skin areas being tested. The display 5 may be a touch screen, in which case the subject touches the diagram where and when a heating sensation is detected. Alternatively, the subject may touch the display with a pressure stick, light pen or light gun, or move a cursor on the screen using a mouse, trackball, touchpad, joystick, eye tracking device, or voice recognition system. The user feedback device is also under to the control of the CPU via a communication link 4, which again, may be a wired or wireless link. The system 2 may further comprise a connection 6 to a communication network, such as a telephone network or computer network, such as the Internet or a local access network (LAN), for telemedicine applications.

Figure 2:
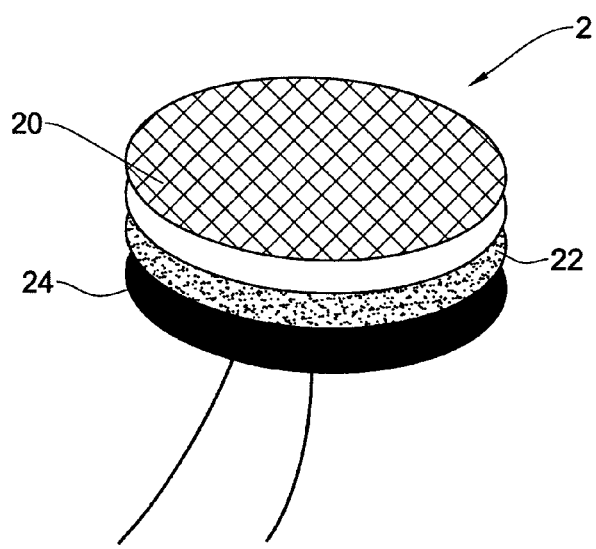
FIG. 2 shows a stimulator configured to deliver thermal energy to a skin region for use in the system of FIG. 1.

FIG. 2 shows an exemplary stimulator 2a in accordance with one embodiment that may be used for the stimulator 2 in the system 1. The stimulator 2a has a superior layer comprising a temperature sensor 20 that contacts a skin region of a body extremity applied to the platform 1. The temperature sensor 20 may be a thermistor or a resistance temperature detector (RTD) configured to measure the temperature of the skin region in contact with it, preferably, with accuracy of about ±1° C., although a more accurate temperature sensor may be used. A mid-layer of the stimulator 2 is made of a heat conducting material 22, such as a metal, and a bottom layer comprises a heating element 24, such as a thermofoil heater. The stimulator 2a is thus configured to heat the skin region in contact with it while simultaneously measuring the temperature of the same skin region.

Figure 5:
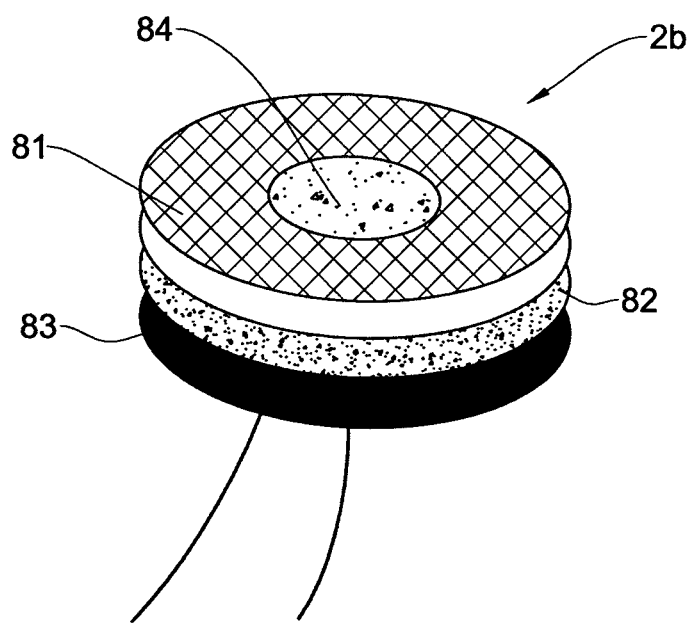
FIG. 5 shows a stimulator configured to deliver thermal energy and vibrational energy to a skin region for use in the system of FIG. 1.

FIG. 5 shows a stimulator 2b another embodiment of a stimulator 2 which can be used in the system 10 to deliver thermal energy and vibrational energy. The stimulator 2b has a superior layer comprising an annular temperature sensor 81 surrounding a vibrator 84. An inferior layer contains an annular heating element 83, such as a thermofoil heater. Between the superior layer and the inferior layer is a heat conducting layer 82. The stimulator 2b is thus configured to heat the skin region in contact with it while simultaneously measuring the temperature of the same skin region. In addition, the stimulator is configured to deliver vibrational energy to the same skin region, either simultaneously with delivery of thermal energy, or sequentially with the delivery of thermal energy.

Each stimulator communicates with the CPU 3 via a link 26 included within the communication link 7. Link 26 serves to activate the heating element 24 as well as to transmit a signal from the temperature sensor 20 to CPU 3 indicative of the temperature of the skin region in contact with the stimulator 2. The diameter of an individual stimulator 2 may range, for example, between 0.1 and 2 cm and the distance between adjacent stimulators in the array may range between 0.1 and 1 cm.

The system 2 may have a stand-by mode in which the CPU is hibernating, the heating elements 24 are all off, and the user feedback device is also off. In the stand-by mode, the system 2 operates on a minimal energy consumption that allows it just to scan the temperature detected in each of the temperature sensors 20.

Figure 3:
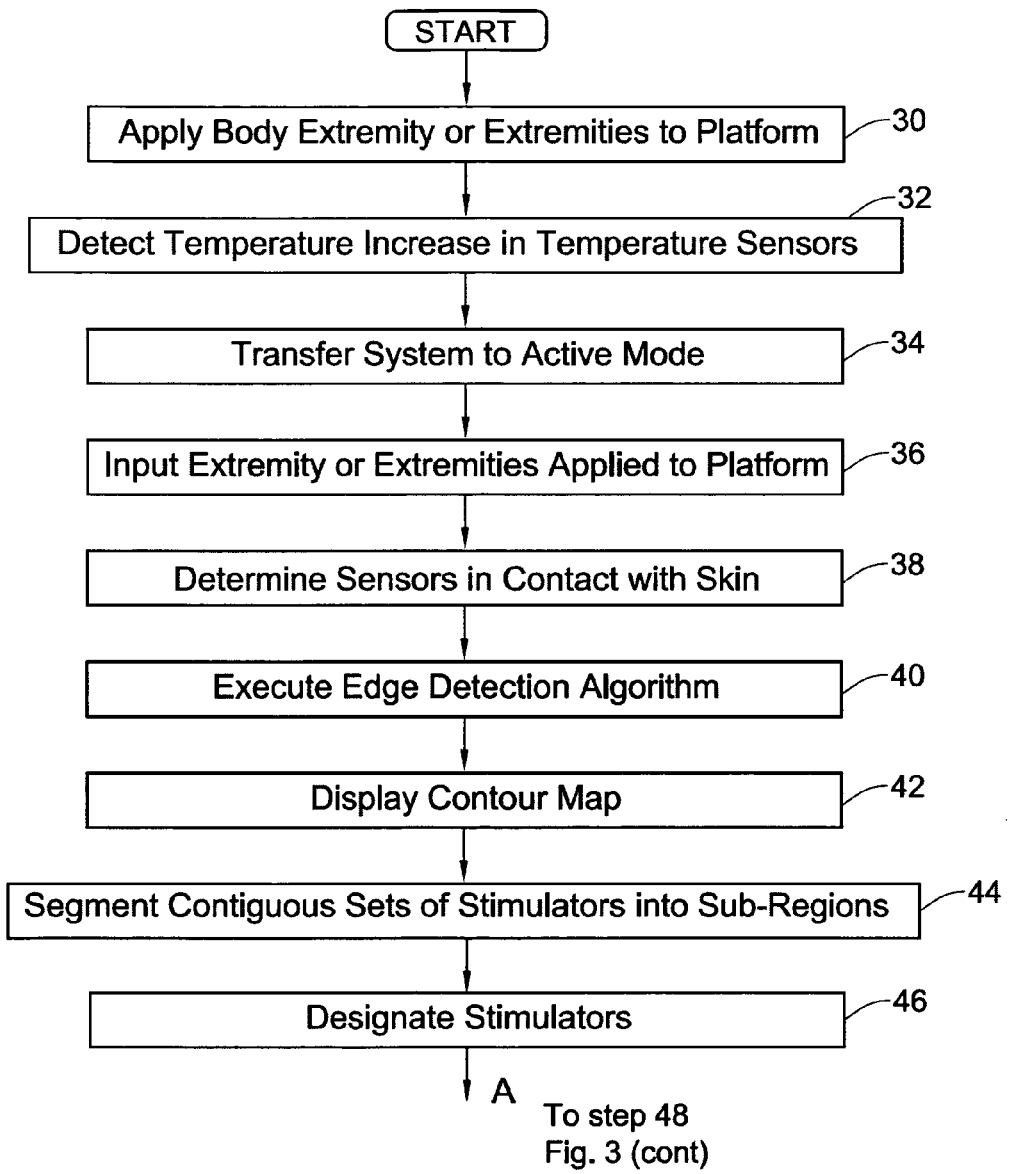
FIG. 3 shows a flow chart diagram for detecting neuropathy in accordance with one embodiment of the invention.
Figure 3:
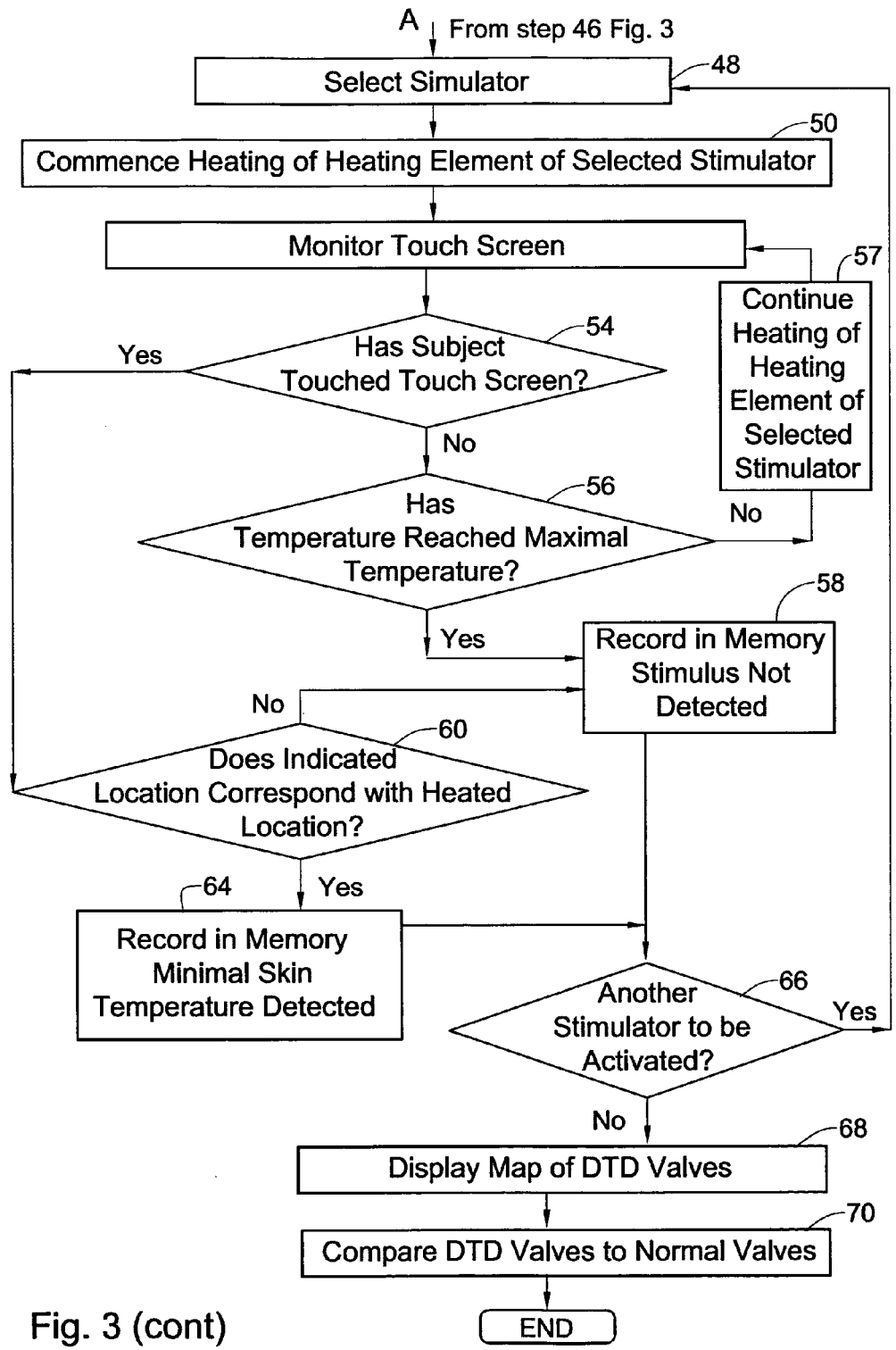

FIG. 3 shows a flow-chart for a method of detecting neuropathy in skin areas in accordance with one embodiment of this aspect of the invention.

Figure 4A:
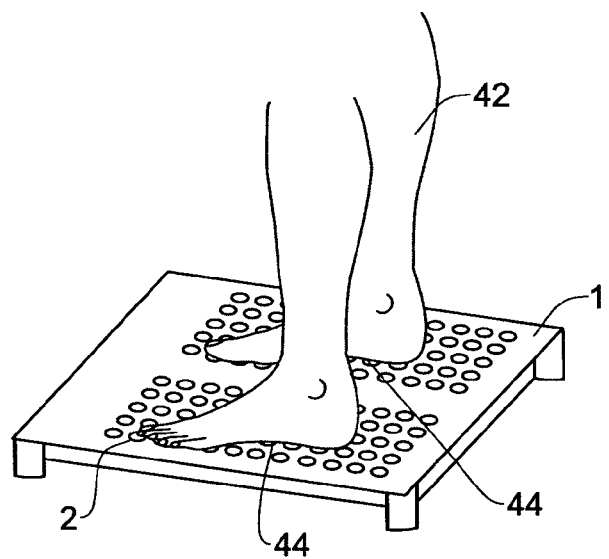
FIG. 4a shows detection of neuropathy in feet.
Figure 4B:
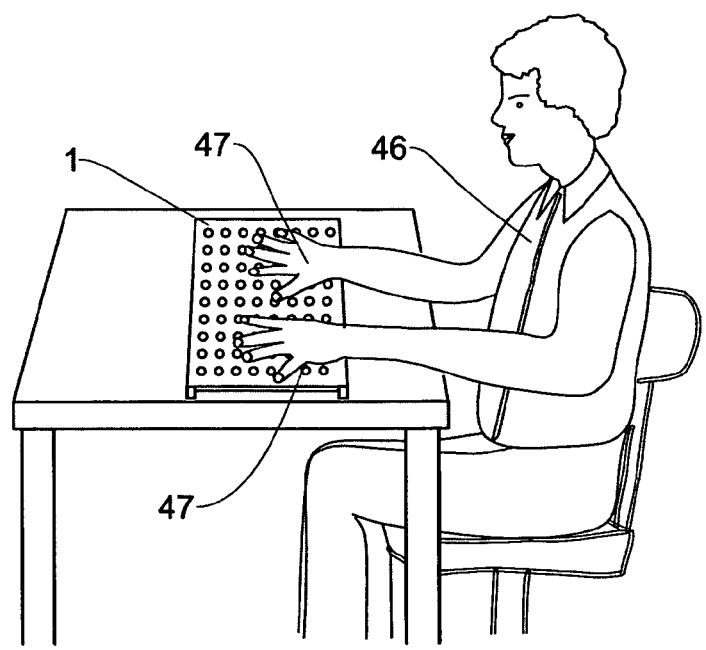
FIG. 4b shows detection of neuropathy in hands, in accordance with one embodiment of the invention.

In step 30, a subject applies one or more skin areas to the surface 21 over the array of stimulators 2. FIG. 4a shows the platform 1 upon which a subject 42 is standing so as to apply at least parts of the soles 44 of his feet to the array of stimulators 2. FIG. 4b shows the platform 1 upon which a subject 46 has applied at least parts of the palms 47 of his hands to the array of stimulators 2. After application of the skin areas to the platform 1, the temperature of the temperature sensors 20 in the stimulators 2 in contact with the skin area or areas increases from the ambient temperature to the local skin temperature. As mentioned above, the CPU 3 may continuously scan the temperature detected by each temperature sensor 20 of the stimulators 2. Referring again to FIG. 3, when the CPU 3 detects a temperature increase in one or more of the temperature sensors 20 (step 32), this is an indication that one or more skin areas has been applied to the platform 1, in response to which the CPU transfers the system 10 from the stand-by mode to an active mode (step 34). Alternatively, the system may be turned on manually, for example, by an on/off switch. Next, in step 36, the user may use the input device 9 to input the skin area or areas applied to the platform 1. The input may be, for example, left hand, right hand, both hands, left foot, right foot, or both feet.

After allowing a few seconds for the temperature sensed by each temperature sensor 20 to reach steady state temperature, the CPU 3 determines, from the sensed temperatures, the specific stimulators 2 in contact with skin areas and not exposed to ambient air (the stimulators hotter than the ambient temperature) (step 38). In step 40, the CPU 3 determines the contours of the skin area in contact with the platform, e.g. by executing an edge detection algorithm, in order to identify contiguous subsets of stimulators 2 in contact with the applied skin areas. Then, in step 42, CPU 3 displays on the screen 5 a contour map 8 of the skin areas applied to the platform 1. The contour map 8 includes the boundary 19 of each skin area applied to the platform 1, and the boundaries 13 of the contiguous sets of stimulators 2 in contact with the skin area or areas (See FIG. 1). Next, in step 44, one or more of the contiguous sets of stimulators 2 in contact with the skin area or areas may be segmented by the CPU 3 into predetermined sub-areas. For example, as shown in FIG. 1, the boundary 19 of each foot in the contour map may be divided into three sub-areas, a sub-area 13 representing a hindfoot, a second sub-area 15 representing a midfoot, and a third sub-area 17 representing a forefoot. The forefoot region 17 can then be further divided into three sections 21, whereas each section represents a site on the sole of the foot between two adjacent metatarsal heads. In step 46, a stimulator element 2 is designated in each of one or more sub-areas. For example, for a foot, the designated stimulators may be a stimulator applied to the hindfoot region, to the midfoot (lateral arch), to three points between adjacent metatarsal heads, and to a point on the big toe.

Now, in step 48, a stimulator 2 is selected from among the stimulators 2 designated in step 46. This stimulator may be selected randomly, but may be determined by any predetermined selection pattern. In step 50, heating of the heating element 24 of the selected stimulator by the CPU 3 commences. The rate of heating of a stimulator may range, for example, between 0.1 and 10 C.°/sec.

The subject is instructed, as soon as the subject feels a warm sensation in his skin, to indicate by the feedback device at the location in the contour map 8 indicative of the location in his skin where the subject feels the warm sensation. If the feet are being examined, as shown in FIG. 4, the subject's hands are free to operate the feedback device. If the hands are being examined, each hand can be checked individually so that the free hand can operate the feedback device. With commencement of the heating of the selected stimulator in step 48, the CPU in step 52 simultaneously monitors the temperature of the skin region in contact with the selected stimulator, as determined by the temperature sensor 20 of the selected stimulator. In step 54 it is determined whether the subject has indicated a heat sensation. If not, then in step 56 it is determined whether the temperature of the skin region has reached a predetermined maximal temperature. The predetermined temperature is typically below 45° C., which is safe and painless even with prolonged exposure, although other maximal temperatures may be used to meet the needs of specific subjects. If it is determined in step 56 that the maximal temperature has been reached (without the subject indicating a heating sensation), then in step 58 the CPU records in the memory 11 that the stimulus was not detected by the subject. If at step 56, it is determined that the maximal temperature has not been reached, then the process proceeds to step 57 with continuing of the heating of the heating element of the selected stimulator, and then returns to step 52 with the monitoring of the skin temperature and feedback device. If at step 54 it is determined that the subject has identified the heated site, the process continues to step 60 where it is determined whether the location indicated by the subject using the feedback device corresponds with the location that was heated. If no, the process proceeds to step 58 with recording in the memory 11 that the patient failed to detect the stimulation. If yes, the CPU 3 records in the memory the difference between the initial temperature sensed on the skin of the patient before heating was applied, and the temperature at that location at the time of the patient's response as determined by the stimulator's heating element 24 at the time indicted by the subject (step 64). This detectable temperature difference (DTD) is a measure of the localized heat perception of the patient. This recorded temperature represents the minimal heat sensation sensible by the subject at the skin region in contact with the selected stimulator. During the examination, the patient does not receive feedback as to whether on the identified location was correct, or what the extent of his temperature perception sensitivity was.

From the recording steps 58 and 64, the process continues with step 66 where it is determined whether another stimulator is to be selected. If yes, the process returns to step 48 with the selection of another stimulator. The process may be repeated until all stimulators in contact with the subject's skin have been heated. When two extremities are stimulated, the heated stimulators may alternate between the two extremities. If in step 66 it is determined that another stimulator is not to be activated, the process continues with step 68 where a map of DTD values is superimposed on the contour map 8, thereby providing a quantitative measure of the neuropathy condition. The process then continues to step 70 where the value of DTD at each location may be compared to a normative database from age-matched control subjects (there is evidence that temperature perception is age-dependent). The deviation from the norm may be presented for each location on similar masked footprints or handprints, e.g. using a z-score to indicate how many standard deviations a measurement deviates above or below the mean of an age-matched population of controls. Additionally, DTD values of a subject may be compared with previous DTD measurements from the same subject for follow-up purposes. The process then terminates.

The system and method of the invention do not involve strapping sensors to the skin surface, or manually applying sensors to the skin surface. The temperature sensitivity data are acquired under physiological loading (standing on the platform or sitting so that the feet rest on the platform for a foot examination, and resting the hands on the platform for a hand examination), which tends to reduce or eliminate variability in the response due to variability in the pressure to which the hands or feet are applied to the stimulators, as occurs when sensors are strapped to the skin surface or are manually applied to the skin surface.

The invention claimed is:

1. A system for diagnosing or monitoring neuropathy in a user, the system comprising:
   a platform comprising a surface in which a two-dimensional array of stimulators is embedded, each stimulator being configured to stimulate a region of user skin when applied to the platform;
   a user feedback device configured to receive an input from the user about a location in the region of user skin where stimulation caused by one or more stimulators of said two-dimensional array is sensed by the user, and to generate signals indicative of the user input; and
   a computer processing unit (CPU) configured to control the platform and activate said one or more stimulators, and to receive from said user feedback device said signals indicative of the user input, and to process said signals and generate corresponding data.

2. The system according to claim 1 wherein said two-dimensional array of stimulators comprise at least one stimulator comprising:
   (i) a heating element configured to heat the region of user skin being in contact with the platform; and
   (ii) a temperature sensor configured to sense the temperature of the region of user skin being in contact with the platform.

3. The system according to claim 1 wherein said two-dimensional array of stimulators comprises at least one stimulator comprising a vibrator configured to deliver a vibration to the region of user skin in contact with the platform.

4. The system according to claim 1 wherein said two-dimensional array of stimulators comprises at least one stimulator comprising:
   (a) a heating element configured to heat the region of user skin in contact with the platform;
   (b) a temperature sensor configured to sense the temperature of the region of user skin in contact with the platform; and
   (c) a vibrator configured to deliver a vibration to the region of user skin being in contact with the platform.

5. The system according to claim 1, wherein said CPU is configured to process the signals received from the user feedback device indicative of the user input about the location in the skin surface where stimulation caused by the one or more stimulators is sensed, and record at least one of the following: data indicative of magnitude of minimal sensation sensible by the user, data indicative of whether a predetermined magnitude of stimulation is not sensed by the user at said location, and data indicative of whether the user indicates wrong stimulation location.

6. The system according to claim 1 wherein the user feedback device is selected from the following: a touch screen, a pointing device, an eye-tracking-activated device and a voice-command-activated device.

7. The system according to claim 6 further comprising a display displaying a contour of surface of the region of user skin being stimulated.

8. The system according to claim 2 or 4 wherein said CPU is configured to:
   (a) monitor a skin temperature of the region of user skin in contact with the platform; and
   (b) control operation of the heating element of any one or more of the stimulators.

9. The system according to claim 3 wherein said CPU is configured to activate the vibrator of any one or more of the stimulators at a selectable magnitude.

10. The system according to claim 8 wherein the CPU is further configured to determine sets of contiguous stimulators from said two-dimensional array of stimulators aligned with the region of user skin being in contact with the platform.

11. The system according to claim 8 wherein the CPU is further configured to determine for each of one or more of the stimulators a detectable temperature difference of the region of user skin being in contact with the platform.

12. The system according to claim 11 wherein the CPU is further configured to compare one or more perceived stimulation levels to a predetermined normative perceived stimulation level.

13. The system according to claim 1 wherein the platform surface is a planar surface.

14. The system according to claim 1 for use in detecting neuropathy in a body extremity.

15. The system according to claim 14 wherein the body extremity is a hand or foot.

16. A method for diagnosing or monitoring neuropathy in a user, the method comprising:
(a) applying a user body part to a platform such that a skin region of the body part contacts a surface of the platform in which a two-dimensional array of stimulators is embedded;
(b) activating at least one of the stimulators;
(c) receiving data indicative of user input to a user feedback device indicative of a magnitude of minimal stimulation at which the stimulation caused by the stimulator is sensed by the user;
(d) comparing the magnitude of minimal stimulation to a predetermined threshold stimulation;
(e) detecting neuropathy in the skin region in contact with the stimulator if (i) the determined minimal stimulation is above the predetermined threshold, or (ii) if a stimulation is not sensed by the user in the skin region in contact with the stimulator before a magnitude of the stimulation reaches a predetermined maximal magnitude;
(f) repeating steps (b) to (e) as required, each time selecting a different stimulator.

17. The method according to claim 16 wherein at least one stimulator comprises:
(i) a heating element configured to heat a skin region in contact with the stimulator;
(ii) a temperature sensor configured to sense the temperature of the skin region in contact with the stimulator.

18. The method according to claim 16 wherein at least one stimulator comprises a vibrator configured to deliver a vibration to a skin region in contact with the stimulator.

19. The method according to claim 16 wherein at least one stimulator comprising:
(a) a heating element configured to heat a skin region in contact with the stimulator;
(b) a temperature sensor configured to sense the temperature of a skin region in contact with the stimulator; and
(c) a vibrator configured to deliver a vibration to a skin region in contact with the stimulator.

20. The method according to claim 16, wherein the data indicative of the user input further comprises data indicative of a location in a skin surface where a stimulation caused by a stimulator is sensed by the user.

21. The method according to claim 16 wherein the user feedback device is selected from the following: a touch screen, a pointing device, an eye-tracking-activated device and a voice-command-activated device.

22. The method according to claim 16 further comprising displaying a contour of one or more skin areas.

23. The method according to claim 18 further comprising:
(a) monitoring a skin temperature of a skin region in contact with any one or more of the stimulators; and
(b) heating the heating element of any one or more of the stimulators.

24. The method according to claim 19 further comprising activating the vibrator of any one or more of the stimulators at a selectable magnitude.

25. The method according to claim 23 comprising using a user feedback device to generate a signal indicative of a location in a skin surface where a sensation is sensed by the user, and receiving a signal from the user feedback device indicative of a location in a skin surface where a sensation is sensed.

26. The method according to claim 23 further comprising determining sets of contiguous stimulators in contact with a skin surface.

27. The method according to claim 23 further comprising determining for each of one or more of the stimulators a detectable temperature difference of a skin region in contact with the stimulator.

28. The method according to claim 27 further comprising comparing one or more perceived stimulation levels to a predetermined normative perceived stimulation level.

29. The method according to claim 17 wherein the platform surface is a planar surface.

30. The method according to claim 17 for use in detecting neuropathy in a body extremity.

31. The method according to claim 30 wherein the body extremity is a hand or foot.

32. A method for monitoring the effect of a drug on neuropathy in an individual, comprising:
(a) detecting a first extent of the neuropathy in the individual by the method according to claim 16;
(b) administering the drug to the individual; and
(c) detecting a second extent of the neuropathy after administration of the drug to the individual.

* * * * *